United States Patent [19]

Supplee et al.

[11] Patent Number: 6,096,905

[45] Date of Patent: Aug. 1, 2000

[54] TREATMENT OF A COMPOSITION COMPRISING A TRIMETHYLOLALKANE BIS-MONOLINEAR FORMAL

[75] Inventors: Carolyn Supplee, Corpus Christi, Tex.; Tobin J. Marks, Evanston, Ill.; William E. Slinkard; Edward G. Zey, both of Corpus Christi, Tex.

[73] Assignee: Celanese International Corporation, Dallas, Tex.

[21] Appl. No.: 09/324,435

[22] Filed: Jun. 1, 1999

[51] Int. Cl.[7] .................................................. C07D 319/06
[52] U.S. Cl. ............................................................. 549/374
[58] Field of Search ............................................... 549/374

[56] References Cited

U.S. PATENT DOCUMENTS 3,076,854  2/1963  Klein ........................................ 260/637

FOREIGN PATENT DOCUMENTS 142184   6/1980  Germany .
1290036  9/1972  United Kingdom .

*Primary Examiner*—Amelia Owens
*Attorney, Agent, or Firm*—M. Susan Spiering; James J. Mullen

[57] ABSTRACT

A process for treating a composition containing a substantial proportion of trimethylolpropane bis-monolinear formal (TMP-BMLF) or trimethylolethane bis-monolinear formal (TME-BMLF), e.g., a heavy ends residue obtained from the purification of a crude trimethylolpropane (TMP) or trimethylolethane (TME) product, wherein the composition is contacted at an elevated temperature with a strong acid catalyst, e.g., methanesulfonic acid, to produce a composition containing significantly increased amounts of TMP and trimethylolpropane monocyclic formal (TMP-MCF) or TME and trimethylolethane monocyclic formal (TME-MCF) respectively.

21 Claims, No Drawings

TREATMENT OF A COMPOSITION COMPRISING A TRIMETHYLOLALKANE BIS-MONOLINEAR FORMAL

BACKGROUND OF THE INVENTION

1. Field of the Invention

The invention relates to a novel process for treating a composition comprising a trimethylolalkane bis-monolinear formal such as that obtained as a heavy ends residue from the purification of a crude trimethylolalkane product, to obtain useful compounds.

2. Description of the Related Art

Trimethylolpropane (TMP) and trimethylolethane (TME) are well-known chemical commodities used as intermediates in the production of a wide variety of products, e.g., varnishes, alkyd and polyester resins, synthetic drying oils, urethane foams and coatings, silicone lube oils, lactone plasticizers, textile finishes, surfactants, epoxidation products, etc. TMP and TME are made by reacting one mole of n-butyraldehyde or propionaldehyde respectively with an amount in excess of 3 moles of formaldehyde in an aqueous medium and in the presence of an alkaline condensation agent. However, these conditions result in the formation of not only TMP or TME, but also various higher boiling impurities. Thus it is necessary to subject the crude TMP or TME product obtained from the reaction to a purification process including distillation and solvent extraction steps, not only to separate relatively pure TMP or TME from excess formaldehyde, water, and basic condensation agent, but also from the higher boiling impurities.

A critical step in the purification process for obtaining relatively pure TMP or TME from the crude product of the reaction is a vacuum distillation or "flashing" of the bulk of the TMP or TME produced in the reaction, which is thus removed as a vapor from the higher boiling impurities remaining behind as a liquid heavy ends residue. While the residue may still contain some TMP or TME, the percentage of such desirable compound is fairly low and is difficult to recover economically. Furthermore, several of the high boiling impurities produced by the reaction in fairly large amounts have only limited commercial value. Thus, any expedient for treating the heavy ends residue, or any compound present in such residue in large amount, so as to convert at least a portion of such compound to TMP or TME and/or other more valuable compounds, would be very desirable.

U.S. Pat. No. 3,076,854 issued Feb. 5, 1963 to Klein, discloses the purification of crude TMP product by a process comprising extracting the reaction liquor with a water immiscible solvent for TMP, e.g., n-butanol or amyl alcohol, subjecting the extract to further extraction with water to obtain a re-extract containing TMP contaminated with metal formate and polyhydric by-products; separating the aqueous re-extract from the stripped solvent, heating the contaminated TMP with methanol or other lower alkanol and a mineral acid to convert the metal formate to a salt of the added acid, and further treating the aqueous TMP re-extract with an acidic cation-exchange resin to remove metal ions from the solution.

British Patent No 1,290,036 discloses a process for removing trimethylpropane monomethyl formal from a crude TMP product by treating the product with a sulfonic acid cation exchange resin. The trimethylolpropane monomethyl formal decomposes to form trimethylolpropane monocyclic formal and methanol.

German Democratic Republic Patent No. 142184 discloses a process for the recovery of TMP from higher boiling residues comprising adding water and methanol to the residues such that they contain at least 15 wt. % of water or 10–40 wt. % of methanol, pretreating the residues with a cation exchange resin to remove traces of condensation agent contained in the residues, treating the residues under distillation conditions with a highly acidic, highly crosslinked cation-exchange resin with a polystyrene base, and recovering the TMP formed by conventional separation means.

BRIEF SUMMARY OF THE INVENTION

As part of the invention disclosed herein, it has been discovered that a major proportion of the heavy ends residue obtained after removing the bulk of the TMP or TME, excess formaldehyde, water, and basic condensation agent, is a trimethylolalkane bis-monolinear formal having the formula,

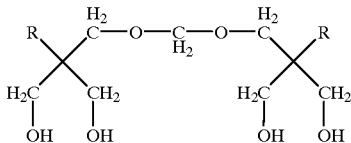

where R is ethyl in the case of trimethylolpropane bis-monolinear formal (TMP-BMLF) CA Index Name1,3-Propanediol, 2,2'-[methylenebis(oxymethylene)]bis[2-ethyl-], CAS No. [93983-16-5] or methyl in the case of trimethylolethane bis-monolinear formal (TME-BMLF) CA Index Name 1,3-Propanediol, 2,2'-[methylenebis (oxymethylene)]bis[2-methyl-], CAS No. [636073-72-5]. Thus, in accordance with the broadest aspect of the invention, a composition comprising a substantial percentage, e.g., at least about 40 wt. %, of TMP-BMLF or TME-BMLF, no more than about 5 wt. % of water, and no more than about 0.5 wt. % of methanol, all percentages based on the total weight of the composition, is contacted with a strong acid catalyst at an elevated temperature and a sufficient period of time to convert a significant amount of said TMP-BMLF or TME-BMLF to TMP or TME and the corresponding trimethylolalkane monocyclic formal having the following formula,

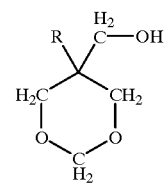

where R is ethyl in the case of trimethylolpropane monocyclic formal (TMP-MCF) CA Index Name 1,3-Dioxane-5-methanol, 5-ethyl, CAS No. [5187-23-5] or methyl in the case of trimethylolethane monocyclic formal (TME-MCF) CA Index Name 1,3-Dioxane-5-methanol, 5-methyl, CAS No. [1121-97-7]. The additional TMP and TMP-MCF or TME and TME-MCF produced by the process have considerably greater value than the TMP-BMLF or TME-BMLF consumed. In many instances the composition treated is a heavy ends residue obtained from a crude TMP or TME product in the course of a purification treatment after the bulk of water, excess formaldehyde, basic condensation agent, and purified TMP or TME have been separated.

DETAILED DESCRIPTION OF THE INVENTION

The composition subjected to the acid treatment of this convention will in many instances contain, for example, at least about 10 wt. %, preferably at least about 20–30 wt. % of TMP-BMLF or TME-BMLF, generally anhydrous to no more than about 5 wt. %, preferably no more than about 1.0 wt. % of water, and no more than about 0.5 wt. %, preferably no more than about 0.1 wt. % of methanol. In addition, the composition being treated will usually contain no more than about 5 wt. %, preferably no more than about 0.6 wt. % of any compound in free form having an atmospheric boiling below that of water, such as formaldehyde. The composition is contacted at an elevated temperature, e.g., about 30° C. to about 300° C. preferably about 90 to about 220° C., with a strong acid catalyst, for a period of time, e.g., of about ½ to about 8 hours, preferably about 1 to about 6 hours, sufficient to convert a significant amount of the TMP-BMLF or TME-BMLF to TMP and TMP-MCF or TME and TME-MCF respectively.

Any strong acid can be used as a catalyst for the process of the invention. While such acid may be an inorganic acid such as sulfuric or phosphoric, it is preferred in most instances to employ an alkanesulfonic acid such as methanesulfonic acid, an arylsulfonic acid such as toluenesulfonic acid, or a sulfonated cation-exchange resin in acid form, e.g., a sulfonated polystyrene-based cation exchange resin. The amount of acid may vary widely, but is often in an amount such that the acidity of conversion reaction is in the range, for example, equivalent to the acidity contributed by the strong acid, less than about 15 wt. % , preferably about 0.3 to about 1.3 wt. %.

Generally a strong acid is added in sufficient amount to result in a pH range of the reaction of less than about 4, and preferably between about 2 and 3, purified BMLF has been found to optimally convert to TMP at about 102° C., pH of about 2.35 in about 4 hours.

As suggested previously, a small amount of water under 5 wt. % may be present in the composition subjected to the acid treatment of this invention. Furthermore, an additional amount of water is produced by the conversion of TMP-BMLF or TME-BMLF to TMP-MCF or TME-MCF respectively. Although not necessary to obtain the advantages of the process, it may be desirable in some instances to keep the amount of water at a lower level than would ordinarily occur. For this purpose a minor amount, e.g. less than about 15 wt. % preferably less than about 10 wt % based on the weight of the composition, of a compound which forms a low boiling azeotrope with water and is substantially immiscible with any of the components of the composition, may be added prior to the initiation of the reaction. Such compound is preferably a hydrocarbon, e.g., cyclohexane, toluene or benzene.

As stated, the process of the invention results in the conversion of a significant amount of the TMP-BMLF or TME-BMLF in the initial composition to TMP and TMP-MCF or TME and TME-MCF respectively. For example, in the case of TMP, it has been found that the product resulting from the acid treatment of the process of the invention may contain at least about 5 wt. %, more TMP-MCF than was present in the initial composition subjected to such acid treatment, based on the weight of the total composition.

Conversely, for example, the amount of TMP-BMLF in the product was found to be reduced by at least about 70 wt. %, of that in the initial composition based on the weight of TMP-BMLF before the acid treatment.

As described previously, the composition subjected to the acid treatment of this invention will in many instances be obtained as a heavy ends residue from a process for producing TMP or TME by reaction of n-butyraldehyde or propionaldehyde with formaldehyde in an aqueous system in the presence of a basic condensation agent such as sodium hydroxide. Such a residue is obtained from the purification of the product of the reaction including the following steps: 1) removal of excess formaldehyde; 2) removal of water; 3) separation of TMP or TME and higher boiling impurities from the liquid being purified, the basic condensation agent and, 4) heating the crude TMP under vacuum to flash off and recover the TMP or TME having a high degree of purity. The remaining residue is the heavy ends residue containing high boiling impurities contemplated for acid treatment under this invention.

When the composition being treated is the heavy ends residue from a TMP process as described previously, such composition usually contains, in addition to TMP-BMLF, TMP in an amount, e.g. less than about 60 wt. %, typically often about 8 to about 20 wt. %; less than about 15 wt. %, typically about 7 to about 10 wt. % of di-trimethylpropane (Di-TMP). The amount of TMP-MCF present in said heavy ends residue is generally lower than the latter compounds, usually less than about 0.1 wt. % and often non-detectable.

In accordance with another aspect of the invention, TMP-MCF or TME-MCF in the composition resulting from the process of the invention is subjected to a transalcoholysis reaction with an excess of a monohydric or dihydric alcohol, e.g., containing 1 to about 6 carbon atoms, at an elevated temperature, e.g., about 30 to about 300° C., in the presence of an acid catalyst, e.g., any of the same acids disclosed previously in connection with the acid treatment of TMP-BMLF or TME-BMLF, to produce additional TMP or TME and an acetal by-product which is often commercially desirable. Thus, for example, the TMP-MCF or TME-MCF in the composition resulting from the acid treatment of the invention may be reacted with excess methanol to produce additional TMP or TME and methylal, useful as a solvent, in organic synthesis, in perfumes, in adhesives, etc., while TMP-MCF or TME-MCF may be reacted with excess ethylene glycol to produce additional TMP or TME and dioxolane, useful as low-boiling solvent and extractant for oils, fats, waxes, dyes and cellulose derivatives.

In addition to their use an intermediate in transalcoholysis reactions to produce additional TMP or TME and other useful compounds, TMP-MCF and TME-MCF may be used to produce useful products by other reactions. Thus, as disclosed in U.S. Pat. Nos. 4,076,727; 4,207,155 and 4,876,368, acrylate and methacrylate esters of TMP-MCF and TME-MCF may be prepared which are useful as reactive monomers in the preparation of coating compositions, plastic films, fibers, plastic coatings and, in particular, as diluents in various unsaturated systems, especially ultraviolet curable coating compositions.

The following examples further illustrate the invention. Small amounts of water were removed from the system utilizing cyclohexane as an acetroping agent.

EXAMPLES 1 AND 1A

In Example 1, a round-bottom flask, equipped with an overhead stirrer, Dean Stark trap with condenser, and a heating system, was charged at ambient temperature with 91.30 grams of a previously analyzed, heavy ends residue obtained from the purification of a crude TMP product as described hereinbefore, 12.53 grams of cyclohexane, and 0.25 grams of methanesulfonic acid as a catalyst. The charge was heated to 98° C. over a period of 90 min., and a sample of product withdrawn and analyzed.

In Example 1A, the procedure of Example 1 was repeated, except that the charge was heated to 110° C. over a period of 275 min.

The compositions of the initial heavy ends residue feed and the treated compositions of Examples 1 and 1A in terms of weight percentages of the most significant components based on the weight of the total composition are shown in Table I.

TABLE I

| Component | Initial Feed | Treated Composition | |
|---|---|---|---|
| | | Ex. 1 | Ex. 1A |
| TMP-MCF | 0.05% | 27.77% | 25.64 |
| TMP | 22.67% | 36.31% | 34.13 |
| TMP-acetate | Undetected | Undetected | 0.15 |
| Di-TMP | 7.65% | 4.39% | 3.54 |
| TMP-BMLF | 41.74% | 0.55% | Undetected |
| DMB | 0.11% | 8.86% | 7.66 |
| MMB | 5.99% | 0.31% | 0.25 |

EXAMPLE 2

The procedure of Example 1 and 1a was followed, except that the initial charge was 462.00 g of heavy ends residue, 69.19 g of cyclohexane and as catalyst, 69.19 g of sulfonated acrylic-polystyrene based cation exchange resin in acid form sold as "Amberlyst 36 (dry)" by Rohm and Haas Co. In employing the solid resin catalyst of this example, the experimental apparatus was modified as follows: The resin was weighed and poured into a "mesh-wire stainless steel basket" which was attached to the stirring shaft. This basket was shaped like an "X" and had four components which were filled with resin. Once filled, the basket was connected to the overhead stirrer motor. Each side of the "basket" had a length of ~7.5 cm, a width of 4 cm and a depth of 1.5 cm and was made using wire with ~42 mesh size. The design and use of the basket allowed heavy ends residue to have intimate contact with the solid acid resin as well as preventing degradation of the solid catalysts due to "grinding" from the stirrer blade.

The charge was heated from 25 to 99.6° C. in 190 min. and kept between 99.5 and 99.8° C. for an additional period of 180 min. (total heating time 370 min.). The composition of withdrawn samples at various time intervals and temperatures are shown in Table II. "N/D" means non-detectable.

TABLE II

| Time (min) | Temp. ° C. | TMP-MCF | TMP | Di-TMP | TMP-BMLF | Water |
|---|---|---|---|---|---|---|
| 0 | 25 | N/D | 10.04 | 7.11 | 58.56 | 0.10 |
| 40 | 83.4 | 0.42 | 10.85 | 7.00 | 52.90 | 0.25 |
| 105 | 95.5 | 23.28 | 26.87 | 4.23 | 5.60 | 0.79 |
| 190 | 99.6 | 32.77 | 28.58 | 4.46 | 0.61 | 0.65 |
| 250 | 99.8 | 32.89 | 28.43 | 4.18 | 0.56 | 0.66 |
| 320 | 99.6 | 32.84 | 28.46 | 4.06 | 0.56 | 0.53 |
| 370 | 99.5 | 31.36 | 27.19 | 3.88 | 0.53 | 0.53 |

EXAMPLE 3

The procedure of Example 2 was followed, except that the initial charge consisted of 709.43 g of heavy ends residue, 96.00 g of cyclohexane and as catalyst, 67.35 g of sulfonated acrylic-polystyrene based cation exchange resin in acid form sold as "Amberlyst 35 (dry)" by Rohm and Haas Co.

The charge was heated from 25 to 95.7° C. in 295 min. and the composition of withdrawn sample at various time intervals and temperatures are shown in Table III.

TABLE III

| Time (min) | Temp. ° C. | TMP-MCF | TMP | Di-TMP | TMP-BMLF | Water |
|---|---|---|---|---|---|---|
| 0 | 25 | N/D | 10.04 | 7.11 | 58.56 | 0.10 |
| 38 | 73.9 | N/D | 10.38 | 7.31 | 57.54 | 0.28 |
| 72 | 83.3 | 14.81 | 25.07 | 4.05 | 11.02 | 1.39 |
| 130 | 91.6 | 34.06 | 30.64 | 4.81 | 0.63 | 1.03 |
| 175 | 93 | 33.24 | 30.03 | 4.52 | 0.61 | 1.25 |
| 245 | 94.3 | 33.65 | 29.77 | 4.20 | 0.62 | 0.63 |
| 295 | 95.7 | 33.5 | 30.02 | 4.30 | 0.62 | 0.89 |

EXAMPLE 4

The procedure of Example 1 was followed, except that the initial charge consisted of 157.85 grams of heavy ends residue, 24.58 grams of cyclohexane and, as catalyst, 0.86 gram of a modified toluenesulfonic acid sold as "Witco TX Acid" by Witco Chemical Corp., containing 1.0 wt. % of moisture and 2.0 wt. % of sulfuric acid, and having a melting point under 15° C., a specific gravity at 25/4° C. of 1.30 and an acid number of 330. The charge was heated from 25 to 200° C. in 182 min. and the compositions of withdrawn samples at various time intervals and temperatures are shown in Table IV.

TABLE IV

| Time (min) | Temp. ° C. | TMP-MCF | TMP | Di-TMP | TMP-BMLF | Water |
|---|---|---|---|---|---|---|
| 0 | 25 | N/D | 10.04 | 7.11 | 58.56 | 0.10 |
| 60 | 100 | 31.39 | 29.62 | 5.07 | 0.78 | 0.20 |
| 75 | 112 | 32.65 | 30.80 | 5.14 | 0.65 | 0.10 |
| 80 | 127 | 32.37 | 31.31 | 5.06 | 0.71 | 0.14 |
| 85 | 143 | 32.38 | 32.22 | 4.55 | 0.62 | 0.11 |
| 98 | 160 | 33.00 | 32.13 | 4.51 | 0.80 | 0.27 |
| 108 | 175 | 34.06 | 31.72 | 4.38 | 0.80 | 0.38 |
| 120 | 185 | 36.61 | 27.89 | 3.76 | 0.82 | 0.45 |
| 151 | 190 | 41.66 | 20.45 | 2.58 | 0.75 | 0.37 |
| 182 | 200 | 46.13 | 17.43 | 2.36 | 0.84 | 0.34 |

EXAMPLE 5

The procedure of Example 4 was followed, except that the initial charge consisted of 186.54 grams of heavy ends residue, 24.82 grams of cyclohexane and 0.92 gram of modified toluenesulfonic acid catalyst. The charge was heated to 121° C. in 138 minutes and kept between 121 and 133° C. for an additional 265 min. for a total heating time of 403 min. The composition of withdrawn samples at various time intervals and temperatures are shown in Table V.

TABLE V

| Time (min) | Temp. ° C. | TMP-MCF | TMP | Di-TMP | TMP-BMLF | Water |
|---|---|---|---|---|---|---|
| 0 | 25 | N/D | 10.04 | 7.11 | 58.56 | 0.10 |
| — | 40 | 2.09 | 17.66 | 6.23 | 39.4 | 0.81 |
| 11 | 50 | 11.91 | 25.97 | 4.13 | 11.61 | 0.62 |
| 17 | 60 | 12.56 | 25.53 | 4.21 | 11.02 | 0.72 |
| 24 | 74 | 16.36 | 26.77 | 4.36 | 8.46 | 0.85 |
| 28 | 80 | 12.76 | 25.91 | 4.23 | 11.62 | 0.79 |
| 59 | 90 | 29.88 | 28.81 | 5.04 | 0.85 | 0.52 |
| 88 | 100 | 31.66 | 29.92 | 4.99 | 0.62 | 0.19 |
| 126 | 112 | 31.80 | 31.71 | 4.51 | 0.73 | 0.12 |
| 138 | 121 | 32.38 | 32.22 | 4.39 | 0.72 | 0.12 |
| 151 | 125 | 32.67 | 32.01 | 4.43 | 0.78 | 0.19 |
| 223 | 125 | 34.8 | 28.71 | 4.04 | 0.78 | 0.36 |

TABLE V-continued

| Time (min) | Temp. ° C. | TMP-MCF | TMP | Di-TMP | TMP-BMLF | Water |
|---|---|---|---|---|---|---|
| 283 | 133 | 34.56 | 28.26 | 3.92 | 0.72 | 0.15 |
| 343 | 121 | 34.22 | 27.6 | 3.76 | 0.65 | 0.17 |
| 403 | 126 | 35.39 | 28.11 | 4.06 | 0.76 | 0.11 |

As indicated in the data shown in the tables of the examples, an acid treatment under the conditions of the invention of a heavy ends residue obtained from the purification of a crude TMP product containing a substantial percentage of TMP-BMLF results in the conversion of the bulk of the TMP-BMLF to TMP and TMP-MCF. A corresponding acid treatment of the heavy ends residue obtained from the purification of a crude TME product results in a similar transformation of the TME-BMLF in such residue to TME and TME-MCF.

We claim:

1. A process comprising contacting a composition containing a substantial percentage of trimethylolpropane bis-monolinear formal or trimethylolethane bis-monolinear formal, no more than about 5 wt. % of water, and no more than about 0.5 wt % of methanol, with a strong acid catalyst at a temperature of from about 30° C. to about 300° C. for a period of time of from about ½ to about 8 hours to convert a significant amount of said trimethylolpropane bis-monolinear formal or trimethylolethane bis-monolinear formal to trimethylopropane and trimethylopropane monocyclic formal or trimethylolethane and trimethylolethane monocyclic formal, respectively.

2. The process of claim 1 wherein said composition is a heavy ends residue obtained by removing the bulk of water, excess formaldehyde, basic condensation agent, and purified trimethylpropane or trimethylolethane in the course of purifying a crude trimethylpropane or trimethylolethane product obtained by reacting n-butyraldehyde or propionaldehyde respectively with formaldehyde in an aqueous medium and in the presence of an alkaline condensation agent.

3. The process of claim 2 wherein said heavy ends residue contains trimethylolpropane bis-monolinear formal and is obtained in the course of purifying a crude trimethylpropane product.

4. The process of claim 3 wherein said heavy ends residue contains at least about 10 wt. % of trimethylolpropane bis-monolinear formal.

5. The process of claim 4 wherein said heavy ends residue contains at least about 20 wt. % of trimethylolpropane bis-monolinear formal, no more than about 1 wt. % of water, and no more than about 0.1 wt. % of methanol.

6. The process of claim 3 wherein said elevated temperature is from about 90 to about 220° C. and said period of time is from about 1 to about 6 hours.

7. The process of claim 1 wherein said acid catalyst is an alkanesulfonic acid, an arylsulfonic acid, or a sulfonated cation-exchange resin in acid form.

8. The process of claim 7 wherein said acid catalyst is selected from the group of sulfuric acid or phosphoric acid.

9. The process of claim 8 wherein said acid catalyst is methanesulfonic acid.

10. The process of claim 8 wherein said acid catalyst is a toluenesulfonic acid.

11. The process of claim 7 wherein said acid catalyst is a sulfonated polystryrenebased cation exchange resin in acid form.

12. The process of claim 1 wherein said acid catalyst is present in an amount of from about 0.1 to about 15 wt. %.

13. The process of claim 12 wherein said range is about 0.3 to about 1.3 wt. %.

14. The process of claim 3 wherein less than about 15 wt. % based on the weight of total composition of a hydrocarbon and is substantially immiscible with any of the components of the composition, is added to said heavy ends residue fed to said process.

15. The process of claim 14 wherein said hydrocarbon is cyclohexane.

16. The process of claim 3 wherein said heavy ends residue being fed to the process also contains less than about 60 wt. % of trymethylpropane.

17. The process of claim 1 wherein the trimethylolpropane monocyclic formal or trimethylolethane monocyclic formal in the composition resulting from such process is subjected to a transalcoholysis reaction with excess monohydric or dihydric alcohol at an elevated temperature and in the presence of an acid catalyst to produce trimethylolpropane or trimethylolethane respectively and an acetal by-product.

18. The process of claim 17 wherein said alcohol is methanol and said acetal by-product is methylal.

19. The process of claim 17 wherein said alcohol is ethylene glycol and said acetal by-product is dioxolane.

20. The process of claim 17 wherein the alcohol is linear or branched.

21. The process of claim 20 wherein the alcohol is selected from 1-propanol, 2-propanol, or 2-bromopropanol.

* * * * *